United States Patent [19]

Buus et al.

[11] 4,044,024

[45] Aug. 23, 1977

[54] THIAXANTHENE DERIVATIVES

[75] Inventors: Jorn Lasse Martin Buus, Bjaeverskov; Niels Lassen, Gentofte; Allan Johan Bigler, Copenhagen, all of Denmark

[73] Assignee: Kefalas A/S, Denmark

[21] Appl. No.: 593,559

[22] Filed: July 7, 1975

Related U.S. Application Data

[63] Continuation-in-part of Ser. No. 421,279, Dec. 3, 1973, abandoned.

[30] Foreign Application Priority Data

Dec. 8, 1972 United Kingdom .............. 56910/72

[51] Int. Cl.$^2$ ........................................ C07D 335/20
[52] U.S. Cl. .................................. 260/328; 542/471; 260/268 TR; 260/293.57
[58] Field of Search ........... 260/268 TR, 328, 240 TC

[56] References Cited

U.S. PATENT DOCUMENTS

| | | | |
|---|---|---|---|
| 2,951,082 | 8/1960 | Sprague et al. | 260/268 TR |
| 3,282,930 | 11/1966 | Craig et al. | 260/268 TR |
| 3,310,553 | 3/1967 | Bloom et al. | 260/268 TR |

FOREIGN PATENT DOCUMENTS

| | | | |
|---|---|---|---|
| 932,494 | 7/1963 | United Kingdom | 260/268 TR |

*Primary Examiner*—Donald G. Daus
*Assistant Examiner*—Jose Tovar
*Attorney, Agent, or Firm*—Gordon W. Hueschen

[57] ABSTRACT

Fluoro-substituted thiaxanthene derivatives as well as their non-toxic pharmaceutically acceptable acid addition salts having pronounced neuroleptic properties and a relatively low degree of undesired side effects, methods of preparation of said derivatives, pharmaceutical compositions containing same which may be administered to animals, including human beings, orally or parenterally.

4 Claims, No Drawings

THIAXANTHENE DERIVATIVES

This application is a continuation-in-part of application Ser. No. 421,279, filed Dec. 3, 1973, now abandoned.

BACKGROUND OF THE INVENTION

In the past, several drugs having a tricyclic structure have been found useful in the treatment of severy psychotic disorders, especially of the schizophrenic type. Most of these derivatives are phenothiazine derivatives which are substituted in the 2-position of one of the benzene rings and having at the ring nitrogen atom an alkyl side chain substituted with a tertiary amino group at a position three carbon atoms from the ring nitrogen atom. The tertiary amino group may also form part of a heterocyclic ring system and such a system, especially the piperazine ring system, is present in several very strong neuroleptic drugs. Also thiaxanthenes substituted in equivalent positions with similar groups and having an unsaturated bond have been found useful in the treatment of psychoses. It is a well-known fact that the aforementioned mono-substituted phenothiazines or thiaxanthenes cause severe extrapyrimidal symptoms in many patients, which makes further treatment difficult or impossible.

SUMMARY OF THE INVENTION

According to the present invention it has now surprisingly been found that certain thiaxanthene derivatives which are substituted in the 2-position with groups of the ordinary type, in the 6-position with a fluorine atom and, containing in the alkyl- or alkylidene side chain a piperazine or piperidine group, have neuroleptic properties of the same level as the known thiaxanthene-neuroleptics but a much lower level of pharmacological effects associated with extrapyrimidal symptoms when they are evaluated according to standard reliable published test methods. Moreover, especially some of the alkylidene substituted compounds have been showed to have a much longer effect when administered to test animals as compared with compounds having no fluorine atom at the 6-position.

The novel thiaxanthenes according to the present invention may be represented by the following general formula:

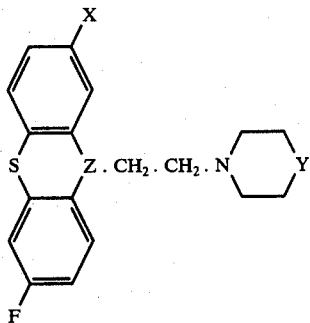

wherein X is —Cl,—CF$_3$ or —SO$_2$.N(CH$_3$)$_2$, Z is >CH.CH$_2$ or >C=CH—, and Y is >NH, >N.CH$_3$, >N.CH$_2$.CH$_2$OH, N.CH$_2$.CH$_2$OAc, >CH.CH$_3$ , >CH.CH$_2$.CH$_2$OH or >CH.CH$_2$.CH$_2$OAc, wherein —Ac is an acyl radical or an aliphatic carboxylic acid having one to seventeen carbon atoms inclusive.

Preferred compounds of this invention are those of Formula I in which X is —CF$_3$ and Y is >N.CH$_2$.CH$_2$OH, >N.CH$_2$.CH$_2$OAc, >CH.CH$_2$.CH$_2$OH or >CH.CH$_2$.CH$_2$OAc.

This invention also includes pharmaceutically acceptable salts of the above defined bases formed with non-toxic organic and inorganic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, embonic, succinic, bis methylene-salicyclic, methanesulfonic, ethanedisulfonic, acetic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids as well as the 8-halotheophyllines, for example 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts which is wellknown in the art. - The compounds of Formula I and the non-toxic acid addition salts thereof may be administered both orally and parenterally, for example in the form of tablets, capsules, powders, syrups or solutions for injection.

According to the method of the invention the thiaxanthenes of Formula I are prepared by a. dehydrating a thiaxanthenol of the formula:

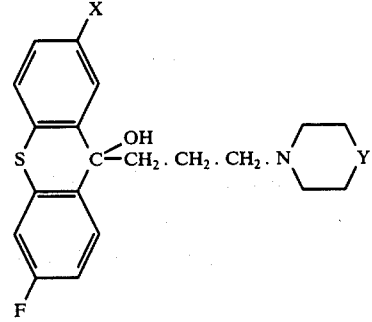

wherein X and Y are as previously defined to obtain a compound of Formula I wherein Z is >C=CH— and, if desired, reducing this compound catalytically to give a compound of Formula I wherein Z is >CH.CH$_2$-, or b. reducing a thiaxanthenol of Formula II to obtain a compound of Formula I wherein Z is >CH.CH$_2$-, or c. reacting a compound of the formula:

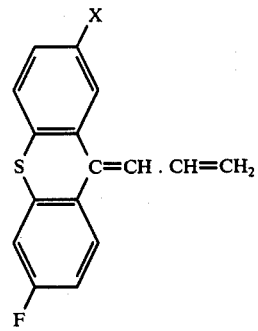

wherein X is as previously defined, with an amine of the formula:

wherein Y is as previously defined and, if desired, reducing the obtained compound of Formula I, wherein Y is >C=CH— to obtain a compound of Formula I wherein Z is >CH.CH-, or d. reacting a compound of the formula:

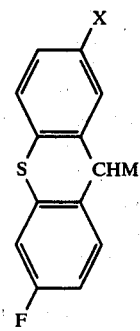

wherein X is as defined above and M is an alkali metal with a reactive ester of a compound of the formula:

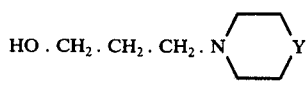

wherein Y is as defined above and a hydroxy-group optionally present therein is protected, and isolating the compound of Formula I wherein Z is >CH.CH$_2$- after removal of any protecting group, or e. reacting a compound of the formula:

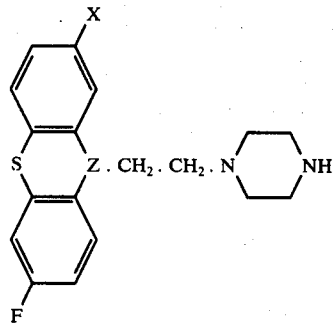

wherein X and Z are as defined above, with a methylating agent or ethylene oxide in order to obtain compounds of Formula I wherein Y is >N.CH$_3$ or >N.CH$_2$.CH$_2$OH, or f. reacting a compound of the formula:

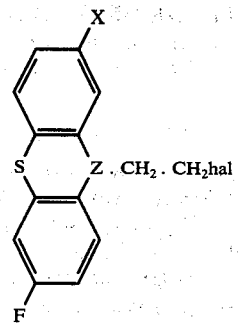

wherein X and Z are as defined above and "hal" is chlorine, bromine or iodine with an amine of the formula:

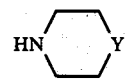

wherein Y is as defined above, or g. reacting a compound of the formula:

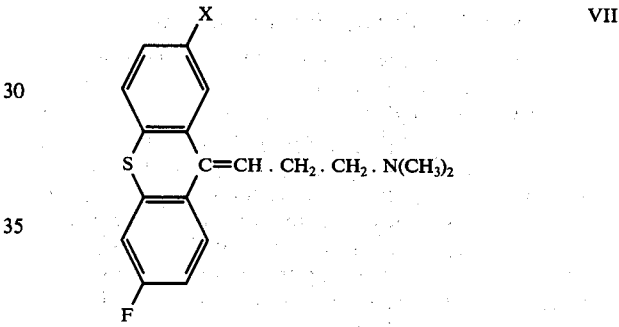

wherein X is as defined above with an amine of the formula:

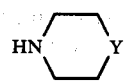

wherein Y is as defined above to obtain a compound of Formula I wherein Z is >C=CH-, and isolating the compound of Formula I as the free base or a non-toxic acid addition salt thereof and, if desired, esterifying any hydroxy group present with a reactive derivative of an aliphatic carboxylic acid having 1 - 17 carbon atoms inclusive, and, if desired, when Z is >C=CH- separating the individual isomers thereof in conventional manner.

In method (a) the dehydration step is advantageously effected by heating with hydrogen chloride in an organic solvent such as an alcohol or chloroform. However, other reagents conventionally used for dehydrating tertiary alcohols can also be employed, e.g. phosphous oxychloride, p-toluene sulfochloride, sulfuric acid, zinc chloride, potassium bisulfate and the like, in inert organic solvents, e.g. chloroform and methylene chloride. The reduction step is preferably carried out with hydrogen iodide or any modification thereof which will produce hydrogen iodide in situ. If a group sensitive to the action of hydrogen iodide is present, however, the hydrogenation may be carried out in the presence of a hydrogenation catalyst such as platinum oxide or palladium-on-charcoal.

In method (b) the reduction of the tertiary hydroxy compound is advantageously carried out by dissolving it in a solvent such as acetic acid, adding the reducing agent, preferably hydrogen iodide, and then refluxing until the reaction is completed. A reducing agent for iodine, such as phosphorus or hypophosphorus acid can, if desired, be employed to reconvert the iodine liberated to hydrogen iodide.

Method (c) is described in U.S. Pat. No. 3,116,291 wherein also the preparation of starting materials similar to the compounds of formula III are described.

In method (d) the alkali metal M is preferably selected from lithium, sodium and potassium, and as reactive esters of the compounds of formula V may, according to the invention, be used the halides, such as chlorides or bromides, or an arylsulfonate such as p-tosylate or phenylsulfonate, in a suitable inert aromatic solvent such as benzene, xylene or toluene. The reaction is preferably carried out in the presence of butyl lithium, phenyl lithium, sodamide, potassium amide, sodium hydride, or the like, which will form the compound of formula IV from the corresponding thiaxanthene.

The methylating agent used in method (e) is preferably selected from methyl iodide and dimethyl sulfate.

Method (g) is described in U.S. Pat. No. 3,149,103 for similar thiaxanthenes.

When preparing esters of compunds of Formula I having a hydroxy group i.e. when Y is >N.CH₂.CH₂OH or >CH.CH₂.CH₂OH the esterifying agent is advantageously an acid halide of the acid in question or an anhydride. As acids may be mentioned acetic acid, propionic acid, butyric acid, valeric acid, enanthic acid, decanoic acid and palmitic acid. Other acids may, however, be used equally.

When Z is >C=CH- the compounds of Formula I are generally obtained as a mixture of the geometric isomers. Mostly the individual isomers do have the desired effects to a different degree. Preferably, therefore, the individual isomers are according to the invention separated in conventional manner, such as by fractional crystallization of a mixture of the bases or an appropriate acid addition salt.

The starting materials of Formula II, III, IV, VI and VII may conveniently be prepared by methods known in the art for the preparation of such compounds, and reference is made to U.S. Pat. Nos. 2,951,982 and 3,282,930 and the two previously mentioned patents where methods suitable for the preparation of starting materials are described in detail. It is to be understood that obvious chemical equivalents and modifications of the methods of the present invention apparent to those skilled in the art fall within the scope of the present invention.

The starting materials of Formula II, III, IV, VI and VII are novel compounds and fall within the scope of the present invention.

The following examples are given to illustrate the methods and products of the present invention but, they are to be understood as exemplary only and are not to be construed as limiting.

EXAMPLE 1

2-Trifluoromethyl-6-fluoro-9-(3-(4-(2-hydroxyethyl)-piperazine-1-yl)propylidene)-thiaxanthene, its isomers, their dihydrochlorides and the dihydro derivative thereof.

The starting material, 2-trifluoromethyl-6-fluoro-9-(3-dimethylamino propylidene)-thiaxanthene, was prepared in the following way:

104 grams of 3-fluorothiophenol and 50 grams of sodium ethanate were dissolved in 500 milliliters of 99% ethanol whereupon 165 grams of 5-trifluoromethyl-2-chlorobenzonitrile were added and the mixture refluxed for 4 hours. Then 165 grams of potassium hydroxide and 30 milliliters of water were added and the refluxing continued for 4 hours. The reaction mixture was dissolved in 4 liters of water and the solution made acid with concentrated hydrochloric acid; filtered, and the filter cake washed and dried in a desiccator. Yield: 250 grams of 2-(3'-fluorophenylthio)-5-trifluoromethyl-benzoic acid.

250 grams of 2-(3-fluorophenylthio-5-trifluoromethylbenzoic acid were dissolved in 1500 milliliters of concentrated sulfuric acid, and the mixture heated to about 65 degrees Centigrade. After cooling the reaction mixture was poured onto crushed ice. The precipitate was filtered off and reprecipitated from acetone-concentrated aqueous ammonia and washed. The precipitate was dissolved in chloroform, the chloroform solution dried over anhydrous potassium carbonate. Upon evaporation of the chloroform 101 grams of 2-trifluoromethyl-6-fluorothiaxanthone were obtained. MP: 195.5° - 196.5° Centigrade.

100 grams of 2-trifluoromethyl-6-fluoro-thiaxanthone were added to 500 milliliters of 2 N dimethylaminopropyl magnesium chloride in tetrahydrofuran and the mixture refluxed for 30 minutes. The reaction mixture was poured onto crushed ice with ammonium chloride. The resulting mixture was extracted with ether, the ether solution washed and dried over anhydrous potassium carbonate. The ether was evaporated and the residue recrystallized from petroleum ether. Yield: 107 grams of 2-trifluoromethyl-6-fluoro-9-(3-dimethylaminopropyl)-thiaxanthene-9-ol which melts at 132.5° - 134 degrees Centigrade. 50 grams of 2-trifluoromethyl-6-fluoro-9-(3-dimethylaminopropyl)-thiaxanthene-9-ol were dissolved in 150 milliliters of glacial acetic acid and 150 milliliters of concentrated hydrochloric acid were added. Then 150 milliliters were distilled off. The residue was poured into ice water and made alkaline with concentrated sodium hydroxide solution. The mixture was extracted with ether, the etherphase dried over anhydrous potassium carbonate and the ether evaporated. The residue was dissolved in acetone and 2-trifluoromethyl-6-fluoro-9-(3-dimethylaminopropylidene)-thiaxanthene precipitated with dry hydrogen chloride. Yield: 42 grams. The α-isomer melts at 248°-250° degrees Centigrade and the β-isomer at 216°-218° degrees Centigrade.

47 grams of 2-trifluoromethyl-6-fluoro-9-(3-dimethylamino-propylidene)-thiaxanthene, 105 grams of N-(2-hydroxyethyl)piperazine and 10 milliliters of 2-propanol were heated at 140°-150° degrees Centigrade for 24 hours. After cooling the mixture was poured into isopropylether-methylenechloride (1:1) whereupon the organic layer was washed with ether, dried over anhydrous potassium carbonate and 2-trifluoromethyl-6- fluoro-9-(3-(4-(2-hydroxyethyl)piperazine-1-yl)propylidene)-thiaxanthene was precipitated as the dihydrochloride with dry hydrogen chloride. It consists of a mixture of the geometric isomers. Yield: 30 grams. MP: 236°–239° degrees Centrigrade.

15 grams of this mixture was recrystallized twice from 200 milliliters of 99% ethanol, whereby 5.5 grams of the most active α-form were obtained as white crystals melting at 240°–242° degrees Centigrade.

30 grams of 2-trifluoromethyl-6-fluoro-9-(3-(4-(2-hydroxyethyl)piperazine-1-yl)propylidene)-thiaxanthene dihydrochloride were dissolved in methanol and reduced catalytically with hydrogen at 110 atmospheres and 100° Centigrade for 2 hours with 6 grams of 10% palladium-on-charcoal as a catalyst. The catalyst was filtered off and the 2-trifluoromethyl-6-fluoro-9-(3-(4-(2-hydroxyethyl)piperazine-1-yl)propyl)-thiaxanthene crystallized out following evaporation of methanol and cooling. Yield: 26 grams. MP: 225°–228° Centigrade.

EXAMPLE 2

2-Trifluoromethyl-6-fluoro-9-(3-(4-(2-hydroxyethyl)-piperazine-1-yl)propyl-thiaxanthene, its dihydrochloride and 2-trifluoromethyl-6-fluoro-9-(3-(piperazine-1-yl)propyl)thiaxanthene and its dioxalate.

40 grams of 2-trifluoromethyl-6-fluoro-9-(3-dimethylaminopropylidene)-thiaxanthene, 80 grams of piperazine and 10 milliliters of 99% ethanol were refluxed for 24 hours. The mixture was dissolved in isopropylether, cooled and filtered and the filtrate extracted with water. The etherphase was dried over anhydrous potassium carbonate and evaporated. The residue was mixed with 40 milliliters of 57% aqueous hydrogen iodide, 80 milliliters of glacial acetic acid, 10 milliliters of water and 8 grams of red phosphorus and refluxed for 18 hours. The reaction mixture was filtered, the filtrate dissolved in water, made alkaline with concentrated sodium hydroxide solution and extracted with ether. The ether phase was washed with water, dried over anhydrous potassium carbonate; the ether evaporated; the residue dissolved in 200 milliliters of 99% ethanol from which the dioxalate of 2-trifluoromethyl-6-fluoro-9-(3-(piperazine-1-yl)propyl)thiaxanthene could be precipitated melting at 181°–183° Centigrade after recrystallization from ethanol; the solution cooled to 10° Centigrade and 10 milliliters of ethylene oxide added. The reaction mixture was left standing for 4 hours and evaporated. The dihydrochloride of 2 -trifluoromethyl-6-fluoro-9-(3-(4-(2-hydroxyethyl)piperazine-1-yl)propyl)-thiaxanthene was precipitated with dry hydrogen chloride in acetone. Yield: 36 grams. MP: 225°–228° Centigrade.

EXAMPLE 3

2-Trifluoromethyl-6-fluoro-9-(3-(4-(2-hydroxyethyl)-piperazine-1-yl)propyl)-thiaxanthene and its dihydrochloride 10 grams of 2-trifluoromethyl-6-fluoro-9-(3-(4-(2-hydroxyethyl)piperazine-1-yl)propylidene-thiaxanthene in the form of the dioxalate (MP: 214°–216° Centigrade), 9-milliliters of 57% aqueous hydrogen iodide, 18 milliliters of glacial acetic acid, 1milliliter of water and 1 gram of red phosphorus were refluxed for 18 hours. The reaction mixture was filtered, the filtrate dissolved in water, made alkaline with concentrated sodium hydroxide solution and extracted with ether. The ether phase was washed with water, dried over anhydrous potassium carbonate and the ether evaporated. From the residue the dihydrochloride of 2-trifluoromethyl-6-fluoro-9-(3-(4-(2-hydroxyethyl)piperazine-1-yl)propyl)-thiaxanthene was obtained as white crystals by precipitation with dry hydrogen chloride in acetone.

Yield: 5 grams. MP: 225°–228° Centigrade.

EXAMPLE 4

2-Trifluoromethyl-6-fluoro-9-(3-(4-(2-hydroxyethyl)-piperazine-1-yl)propyl)-thiaxanthene and its dihydrochloride 4 grams of Li AlH$_4$ were dissolved in 100 milliliters of ether and 13.3 grams of AlCl$_3$ added in an atmosphere of nitrogen. Then a solution of 10.9 grams of AlCl$_3$ and 24 grams of 2-trifluoromethyl-6-fluoro-9-thiaxanthone in tetrahydrofuran was added dropwise. After standing for 30 minutes, 150 milliliters of water were added dropwise followed by 100 milliliters of 6N sulfuric acid. The ether phase was separated, washed with water, dried over anhydrous potassium carbonate and evaporated. The residue was recrystallized from ether-petroleum ether (1:1) and 17 grams of 2-trifluoromethyl-6-fluoro-thiaxanthene obtained as white crystals which melt at 60°–62° Centigrade.

15 grams of 2-trifluoromethyl-6-fluoro-thiaxanthene were dissolved in 100 milliliters of ether, cooled to zero degrees Centigrade, and 40 milliliters of 15% butyllithium in hexane added dropwise in an atmosphere of nitrogen, whereupon the mixture was left standing for 30 minutes. Then the solution of the lithiumsalt was added dropwise to a solution of 39 grams of 3-bromo-1-chloropropane in 100 milliliters of ether and left standing for a further 30 minutes and then refluxed for 30 minutes. Water was added dropwise to the reaction mixture, the etherphase separated, washed with water and dried. The ether was evaporated and the residue distilled at reduced pressure (0.01 mm Hg). 16 grams of 2-trifluoromethyl-6-fluoro-9-(3-chloropropane)-thiaxanthene was thus obtained as a yellow oil.

16 grams of 2-trifluoromethyl-6-fluoro-9-(3-chloropropane)-thiaxanthene and 48 grams of N-(2-hydroxyethyl)-piperazine in 300 milliliters of toluene were refluxed for 16 hours. The reaction mixture was evaporated, the residue dissolved in water and isopropylether added. The isopropylether phase was separated, washed with water, dried and evaporated. The residue was dissolved in acetone and the dihydrochloride of 2-trifluoromethyl-6-fluoro-9-(3-(4-(2-hydroxyethyl) piperazine-1-yl)-propyl)-thiaxanthene was precipitated with dry hydrogen chloride. Yield: 6 grams. MP: 225°–228° Centigrade.

EXAMPLE 5

2-Trifluoromethyl-6-fluoro-9-(3-(4-(2-hydroxyethyl)-piperazine-1-yl)propyl)-thiaxanthene and its dihydrochloride 144 grams of N-(2-methoxyethyl)-piperazine and 157.5 grams of 3-bromo-1-chloropropane were dissolved in 500 milliliters of ethanol and refluxed for 2 hours. The ethanol was evaporated, the residue dissolved in water, the aqueous solution made alkaline with sodium hydroxide solution, the solution extracted with ether, the ether solution separated, washed with water, dried and evaporated, 110 grams of 4-(2-methoxyethyl)-1-(3-chloropropyl)-piperazine was thus obtained as a yellow oil.

15 grams of 2-trifluoromethyl-6-fluoro-thiaxanthene were dissolved in 100 milliliters of ether, cooled to 0° Centigrade and 40 milliliters of 15% butyllithium in hexane added dropwise in a nitrogen atmosphere and thereafter left standing for 30 minutes, whereupon the reaction mixture was refluxed for 30 minutes. Water was added dropwise and the organic phase separated and washed with water, dried over anhydrous potassium carbonate and evaporated. The residue was an oil and consisted mainly of 2-trifluoromethyl-6-fluoro-9-(3-(4-(2-methoxyethyl)-piperazine-1-yl)propylidene)-thiaxanthene. Yield: 22 grams.

22 grams of 2-trifluoromethyl-6-fluoro-9-(3-(4-(2-methoxy-ethyl)-piperazine-1-yl)propylidene)-thiaxanthene and 150 milliliters of concentrated hydrobromic acid were mixed and destilled at 120° Centigrade. After 1 hour further 50 milliliters of concentrated hydrobromic acid were added and distilled and after 2 hours the reaction mixture was cooled, made alkaline with concentrated sodium hydroxide solution, extracted with ether; the ether phase separated, washed with water, and dried over anhydrous potassium carbonate. The working up of the ether solution was as in Example 3. 15 grams of 2-trifluoromethyl-6-fluoro-9-(3-(4-(2-hydroxyethyl)piperazine-1-yl)propyl)-thiaxanthene dihydrochloride were obtained as white crystals which melt at 225°–228° Centigrade.

In equivalent manner were prepared:
2-chloro-6-fluoro-9-(3-(4-(2-hydroxyethyl)piperazine-1-yl)propyl-thiaxanthene dihydrochloride. MP: 232°–235° Centigrade.
2-Dimethylsulfamoyl-6-fluoro-9-(3-(4-(2-hydroxyethyl)-piperazine-1-yl)propyl)-thiaxanthene dihydrochloride.

EXAMPLE 6

2-Trifluoromethyl-6-fluoro-9-(3-(4-methyl-1-piperazinyl)propyl)thiaxanthene and its dihydrochloride.

17 grams of 2-trifluoromethyl-6-fluorothiaxanthene were dissolved in 250 milliliters of dry ether and cooled to 0° Centigrade, whereupon 40 milliliters of 20% butyllithium in hexane were added dropwise. The reaction mixture was left standing for 30 minutes at 0° Centigrade, whereupon 12 grams of 1-methyl-4-(3-chloropropyl)-piperazine were added dropwise and the reaction mixture was left standing for 15 minutes. The reaction mixture was then poured into water and the organic phase separated, washed with water, extracted with dilute acetic acid, the acetic acid solution made alkaline with sodium hydroxide solution, extracted with ether, the ether phase separated, washed with water, dried over anhydrous potassium carbonate, and evaporated. The residue was dissolved in acetone and the dihydrochloride of 2-trifluoromethyl-6-fluoro-9-(3-(4-methyl-1-piperazinyl)propyl)thiaxanthene precipitated with dry hydrogen chloride as white crystals which melt at 270°–272° Centigrade. Yield: 8.7 grams.

EXAMPLE 7

2-Chloro-6-fluoro-9-(3-(4-2-hydroxyethyl)-1-piperazinyl)propyl)thiaxanthene and its dihydrochlorides.

2-Chloro-6-fluorothiaxanthone (MP: 215°–218° Centigrade) was prepared according to the method described in Example 1.

From 15 grams of 2-chloro-6-fluorothiaxanthone and 3-dimethylaminopropyl magnesium chloride in tetrahydrofuran were obtained in well-known manner 15.5 grams of 2-chloro-6-fluoro-9-(3-dimethylaminopropyl)-thiaxanthen-9-ol (MP: 154°–156° Centigrade).

This carbinol splits off water in wellknown manner when treated with glacial acetic acid/concentrated hydrochloric acid (1:1) followed by evaporation of half the volume. The residue was made alkaline with sodium hydroxide solution, extracted with ether, the ether phase washed with water, dried and evaporated. 2-Chloro-6-fluoro-9-(3-dimethylaminopropylidene)-thiaxanthene was isolated as the hydrochloride which melts at 192°–194° Centigrade.

60 grams of 2-chloro-6-fluoro-9-(3-dimethylaminopropylidene)-thiaxanthene, 180 grams of piperazine and 10 grams of 2-propanol were heated together at 140° Centigrade for 18 hours. After cooling the mixture was dissolved in ether, the etherphase extracted with water, dried over anhydrous potassium carbonate and evaporated. The residue consisted mainly of 2-chloro-6-fluoro-9-(3-(1-piperazinyl)propylidene)thiaxanthene and weighed 55 grams.

50 grams of the residue were mixed with 50 grams of 57% aqueous hydrogen iodide, 100 grams of glacial acetic acid and 8 grams of red phosphorus and refluxed for 18 hours. The reaction mixture was filtered, made alkaline with sodium hydroxide solution and extracted with ether. The ether phase was washed with water, dried over anhydrous potassium carbonate, evaporated, dissolved in 99% ethanol and treated with 10% excess of ethylene oxide at 10° Centigrade for 2½ hours. Then the mixture was evaporated, the residue dissolved in acetone and dry hydrogen chloride added, which resulted in the precipitation of 45 grams of the dihydrochloride of 2-chloro-6-fluoro-9-(3-(4-(2-hydroxyethyl)-1-piperazinyl)propyl)-thiaxanthene as white crystals, which melt at 232°–235° Centigrade.

EXAMPLE 8

2-Trifluoromethyl-6-fluoro-9-(3-(4-(2-hydroxyethyl)-piperazine-1-yl)propyl)-thiazanthene palmitic acid ester.

21.6 grams of 2-trifluoromethyl-6-fluoro-9-(3-(4-(2-hydoxyethyl)-pierpazine1-yl)propyl)-thiazanthene were dissolved in 200 milliliters of acetone; 25 grams of palmitic acid chloride were added and the mixture refluxed for one hour. 20 grams of the ester were recovered as an oil.

IR absorption shows: 1170 cm$^{-1}$ s, 1129 cm$^{-1}$ s, 1090 cm$^{-1}$ s 902 cm$^{-1}$ m, 858 cm$^{-1}$ m, 823 cm$^{-1}$ m UV spectrum: Max. 280 nm $E_{1cm}^{1\%} = 1550$.

In equivalent manner was prepared the decanoic acid ester of 2-trifluoromethyl-6-fluoro-9-(3-(4-(2-hydroxyethyl)-piperazine-1-yl)propyl)-thiazanthene.

IR absorption: 1171 cm$^{-1}$ s, 1130 cm$^{-1}$ s, 1091 cm$^{-1}$ s 901 cm$^{-1}$ m, 855 cm$^{-1}$ m, 821 cm$^{-1}$ m UV spectrum: Maximum 282 nm $E_{1cm}^{1\%} = 1765$

EXAMPLE 9

2-Dimethylsulfamoyl-6-fluoro-9-(3-(4-methylpiperazinyl)propyl-thiazanthene and its dihydrochloride.

The intermediate, 2-dimethylsulfamoyl-6-fluoro-9-(3-(4-methylpiperazine-1-yl)propylidene)-thiazanthene, was prepared in the following way:

69 grams of 3-dimethylsulfamoyl-6-bromo-benzoic acid,
31 grams of 3-fluorothiophenol, 24 grams of sodium-carbonate, 350 milliliters of dimethylformamide and 1 gram of Adam's copper catalyst were heated while stirring under reflux for one hour. The mixture was poured into 2 liters of ice water, filtered, the filtrate washed with ether and made acid with concentrated hydrochloric acid. The precipitate was filtered off and dissolved in 2.5 liters of chloroform and the solution dried over anhydrous magnesium sulfate, filtered and evaporated to a volume of about 300 milliliters. Then 500 milliliters of ether were added and the mixture cooled. 67 grams of 2-(3-fluorophenylmercapto)-5-dimethylsulfamoyl-benzoic acid crystallize thereupon as a white crystalline substance which melts at 220°-223° Centigrade. This substance was added while stirring to 500 milliliters concentrated sulfuric acid and the mixture heated at 60°-65° Centigrade until complete solution of the solid material, whereupon the mixture was poured onto crushed ice. The precipitate was filtered off and washed with water. After recrystallization from 500 milliliters of pyridine 41.5 grams of 2-dimethylsulfamoyl-6-fluorothiaxanthone were obtained as a faintly yellow substance which melts at 213°-216° Centigrade.

To a solution of allyl magnesium bromide in 500 milliliters of ether prepared from 60 grams of allyl bromide were added while stirring and cooling 41 grams of 2-dimethylsulfamoyl-6-fluoro-thiaxanthone. The mixture ws heated for one hour under reflux while stirring, whereupon it was poured into ice water. The mixture was made acid with dilute hydrochloric acid and extracted with ether. From the ether phase was obtained 39 grams of 2-dimethylsulfamoyl-6-fluoro-9-(2-propenylidene)-thiazanthene-ol-9 as a white substance melting at 150°-154° Centigrade.

39 grams of 2-dimethylsulfamoyl-6-fluoro-9-(2-propenylidene)-thiazanthene-ol-9were dissolved in 100 milliliters of benzene and 11 milliliters of acetic anhydride and 0.5 milliliters of acetyl chloride added. The mixture was heated to 55° Centigrade and one drop of concentrated sulfuric acid added. In the course of a few minutes a reaction set in, which caused the temperature to rise to about 65° Centigrade. The mixture was heated for 5 minutes on a steam bath, poured onto ice, extracted with ether, the ether phase separated, washed with cold dilute sodium hydroxide solution, dried over anhydrous potassium carbonate, filtered and evaporated. 35 grams of 2-dimethylsulfamoyl-6-fluoro-9-(propene-3-ylidene-1)-thiaxanthene were thus obtained as a yellow oil.

The 35 grams of yellow oil were mixed with 50 grams of N-methyl-piperazine and heated on a steam bath for 18 hours. The mixture was poured into water and extracted with ether. The ether phase was extracted with dilute aqueous acetic acid, the aqueous phase was separated, made alkaline with sodium hydroxide solution and extracted with ether. The ether phase was separated, dried over anhydrous potassium carbonate, filtered and evaporated. 40 grams of 2-dimethylsulfamoyl-6-fluoro-9-(3-(4-methylpiperazine-1yl)-propylidene)-thiaxanthene were obtained as a yellow oil. It is a mixture of the two geometric isomers.

20 grams of this mixture were dissolved in 150 milliliters of diethylether, cooled and left standing. The white crystalline precipitate was sucked off and dried. Yield: 7 grams of the α-form, which after recrystallization from ethanol melts at 165°-167° Centigrade. The corresponding hydrochloride melts at 245°-250° Centigrade after crystallization from ethanol. The α-form was the most active in the pharmacological tests. From the mother liquer obtained from the crystallization of the α-form it was possible to recover the β-form in the form of the hydrochloride which melts at 270°-275° Centigrade.

15 grams of the mixture of isomers were dissolved in 250 milliliters of ethanol and 3 grams of 10% palladium-on-charcoal were added and the mixture hydrogenated at 100° Centigrade and 120 atmospheres for 2 hours. The reaction mixture was cooled and filtered, and a solution of dry hydrogen chloride in ether was added to pH 4. Upon standing 10 grams of the dihydrochloride of 2-dimethylsulfamoyl-6-fluoro-9-(3-(4-methylpiperazine-1-yl)propyl)-thiaxanthene separated out as a white crystalline substance which melts at 265°-270° Centigrade.

EXAMPLE 10

The acetic acid ester of 2-trifluoromethyl-6-fluoro-9-(3-(4-(2-hydroxyethyl)-piperazine-1-yl)propyl)-thiazanthene and its dihydrochloride.

Five grams of 2-trifluoromethyl-6-fluoro-9-(3-(4-(2-hydroxyethyl)-piperazine-1-yl)propyl)-thiazanthene were dissolved in 100 milliliters of acetone whereupon 5 milliliters of acetyl chloride were added. The mixture was heated for 30 minutes on a steam bath. After cooling the mixture was poured into water, made alkaline with sodium hydroxide solution and extracted with ether. The ether phase was washed with water, dried over anhydrous potassium carbonate and evaporated. 4.5 grams of the acetic acid ester of 2-trifluoromethyl-6-fluoro-9-(3-(4-(2hydroxyethyl)-piperazine-1yl)propyl)-thiazanthene were thus obtained as a yellow oil. The dihydrochloride was prepared in the usual way and melted at 208°-211° Centigrade.

EXAMPLE 11

2-Dimethylsulfamoyl-6-fluoro-9-(3-(4-(2-hydroxyethyl)-1-piperidyl)propylidene)-thiazanthene and its oxalate.

When Example 9 was carried out using 4-(2-hydroxyethyl)-piperidine instead of N-methyl-piperazine there was obtained 2-dimethyl-sulfamoyl-6-fluoro-9-(3-(4-(2-hydroxyethyl)-1-piperidyl)propylidene)-thiazanthene as a yellow oil consisting of a mixture of the isomers. One isomer was isolated in the form of the oxalate by crystallization from ethanol and melts at 171°-173° Centigrade. The other isomer was isolated from the mother liquor also in the form of the oxalate which after recrystallization from ethanol melted at 149°-152° Centigrade.

EXAMPLE 12

2-Trifluoromethyl-6-fluoro-9-(3-(4-(2-hydroxyethyl)-1-piperidyl)propylidene)-thiaxanthene, its isomers, oxalates thereof and hydrochlorides.

The starting material, 2-trifluoromethyl-6-fluoro-9-(2-propenylidene)-thioxanthene, was prepared in the following way:
100 Grams of 2-trifluoromethyl-6-fluorothioxanthone were added to a Grignard solution made from 80 grams of allylbromide and 95 grams of magnesium turnings in 500 milliliters of ether. The mixture was refluxed for 15 minutes and after cooling the reaction mixture was poured into an ammonium chloride solution. The etherphase was separated off, extracted three times each with 200 milliliters of water and evaporated in vacuum. The residue was dissolved in 300 milliliters of benzene and a mixture of 35 milliliters of acetic anhydride, 2 milliliters of acetyl chloride and one drop of concentrated sulphuric acid added. The mixture was heated on a steam bath at about 65° Centigrade until the dehydration started and thereafter for further 15 minutes. Then the mixture was poured unto crushed ice, made alkaline with sodium hydroxide solution and extracted with 500 milliliters of ether. The etherphase was washed three times each with 100 milliliters of water, dried over anhydrous magnesium sulphate and evaporated in vacuum. The residue which was a yellow oil consisted of somewhat impure 2-trifluoromethyl-6-fluoro-9-(2-propenylidene)-thioxanthene. Yield: 105 grams.

150 Grams of 2-trifluoromethyl-6-fluoro-9-(2-propenylidene)-thiaxanthene and 300 grams of 4-(2-hydroxyethyl)-piperidine were heated at 90° Centigrade for 17 hours. The mixture was poured into 2 liters of water which subsequently was extracted with 2 liters of ether. The etherphase was separated, washed three times each with 500 milliliters of water, dried over anhydrous magnesium sulphate and evaporated in vacuum. The oxalate was precipitated and recrystallized from acetone. Yield: 118 grams of 2-trifluoromethyl-6-fluoro-9-(3-(4-(2-hydroxyethyl)-1-piperidyl)-propylidene)thiaxanthene oxalate in the form of a mixture of isomers melting at 142°-144° Centigrade.

The pharmacologically inactive beta-isomer was isolated in the form of its oxalate by five recrystallizations from 2-propanol : methanol (1:1) and melts at 150-153 degrees Centigrade.

The pharmacologically active alpha-isomer was isolated by boiling the mixture of oxalates with acetone. By evaporation of the acetone-solution in vacuum a mixture containing about 80% of the active isomer was obtained. The base was precipitated with dilute sodium hydroxide solution and extracted with 200 milliliters of ether, which was washed three times each with 50 milliliters of water, dried over anhydrous magnesium sulphate and evaporated in vacuum. The residue was dissolved in acetone and precipitated with dry hydrogen chloride in ether. The hydrochloride of the active alpha-isomer was obtained as a white crystalline substance which melted at 166-168 degrees Centigrade. The inactive isomer may be converted in part to the active isomer by boiling with a solution containing a strong alkaline substance such as sodium ethylate and isolating the active isomer as described above. The base of the active alpha-isomer was isolated in conventional manner and melted at 128-129 degrees Centigrade.

EXAMPLE 13

2-Trifluoromethyl-6-fluoro-9-(3-(4-(2-hydroxyethyl)-1-piperidyl)propyl)-thiaxanthene, its oxalate and its hydrochloride.

25 Grams of 2-trifluoromethyl-6-fluoro-9-(3-(4-(2-hydroxymethyl)-1-piperidyl)propylidene)thiaxanthene oxalate in the form of a mixture of isomers melting at 142°-144° Centigrade were dissolved in methanol and reduced catalytically with hydrogen at 110 atmospheres and 100° Centigrade for 3 hours with 5 grams of 10% palladium-on-charcoal as a catalyst. The catalyst was filtered off and the oxalate of 2-trifluoromethyl-6-fluoro-9-(3-(4-(2-hydroxyethyl)-1-piperidyl)propyl)-thiaxanthene crystallized out following evaporation of methanol and cooling. Yield: 20 grams. MP: 182°-184° Centigrade.

The corresponding hydrochloride was obtained from ethanolic hydrogen chloride and melted at 118°-120° Centigrade.

EXAMPLE 14

2-Dimethylsulfamoyl-6-fluoro-9-(3-(4-methylpiperidin-1-yl)propylidene)-thiaxanthene, its isomers and hydrochlorides and its dihydroderivative and the hydrochloride thereof.

When Example 9 was carried out using 4-methyl-piperidine instead of N-methyl-piperazine there was obtained two isomers of 2-dimethylsulfamoyl-6-fluoro-9-(3-(4-methylpiperidin-1-yl)propylidene)-thiaxanthene in the form of their hycrochlorides which melt at 220°-222° Centigrade and 188°-191° Centrigrade respectively, and by hydrogenation the hydrochloride of 2-dimethylsulfamoyl-6-fluor-9-(3-(4-methylpiperidine-1-yl) propyl)thiaxanthene which melts at 232°-234° Centigrade.

EXAMPLE 15

2-Chloro-6-fluoro-9-(3(4-(2-hydroxyethyl) piperidin-1-yl)propylidene)-thiaxanthene, isomers thereof and hydrochlorides.

60 Grams of 2-chloro-6-fluoro-9-(3-dimethylamino-propylidene)thiaxanthene, 159 grams of 4-(2-hydroxyethyl)-piperidine and 20 grams of 2-propanol were heated together at 140° Centigrade for 24 hours. After cooling the mixture was dissolved in ether, the etherphase extracted with water, dried over anhydrous potassium carbonate and evaporated. The residue consisted mainly of a mixture of the isomer of 2-chloro-6-fluoro-9-(3-(4-(2-hydroxyethyl)piperidin-1 -yl)-propylidene)thiaxanthene. Yield: 50 grams.

25 grams of this mixture was recrystallized twice from 250 milliliters of 99% ethanol, whereby 7 grams of the betaisomer melting at 143°-146° Centigrade were obtained. From the mother liquor there was obtained by precipitation with hydrogen chloride in ethanol and repeated recrystallizations from ethanol the hydrochloride of the alfa-isomer which melted at 220°-222° Centigrade.

EXAMPLE 16

The palmitic acid ester of the alpha-isomer of 2-trifluoromethyl-6-fluoro-9-(3-(4-(2-hydroxyethyl)-1-piperidyl)propylidene)-thiaxanthene.

When Example 8 was carried out using the alpha-isomer of 2-trifluoromethyl-6-fluoro-9 -(3-(4-(2-hydroxyethyl)-1-piperidyl)propylidene)thiaxanthene instead of 2-trifluoromethyl-6-fluoro-9-(3-(4-(2-hydroxyethyl)-piperazine-1-yl)-propyl)-thiaxanthene the palmitic acid ester of the alpha-isomer of 2-trifluoromethyl-6-fluoro-9-(3-(4-(2-hydroxyethyl)-1-piperidyl)propylidene)-thiaxanthene was obtained as a waxy mass.

Analysis: $C_{40}H_{55}F_4NO_2S$. - Calculated, per cent: C, 69.60; N, 2.03. Found, per cent; C, 68.73; N, 1.77.

Moreover the following compounds were prepared;
2-Chloro-6-fluoro-9-(3-(4-(2-hydroxyethyl)-1-piperidyl) propyl)-thiaxanthene and its citrate;
2-Chloro-6-fluoro-9-(3-(4-methyl-1-piperiazinyl)-propylidene) thiaxanthene and its dihydrochloride;
2-Dimethylsulfamoyl-6-fluoro-9-(3-(4-(2-hydroxymethyl)-1-piperidyl)propyl)-thiaxanthene and its maleate;

2-Dimethylsulfamoyl-6-fluoro-9-(3-(4-methyl-piperidin-1-yl)propylidene)-thiaxanthene and its hydrochloride;

2-Trifluoromethyl-6-fluoro-9-(3-(4-methyl-piperazin-1-yl) propylidene)-thiaxanthene and its dihydrochloride.

The pharmacological testing of the compounds of the present invention consisted of (1) a standard and reliable, published test showing the neuroleptic activity of the compounds in that they antagonize central nervous stimulating compounds such as amphetamine and methylphenidate. The methylphenidate test was selected after it had proved to be a reliable test method on several known neuroleptics and reference is made to Pedersen, V.& Christensen, A.V.: "Methylphenidate antagonism in mice as a rapid screening test for neuroleptic drugs."Acta pharmacol. et toxicol. 1971, 29, suppl. 4, 44.

The test may briefly be described as follows:

1. As animals were used NMRI male mice weighing 18 - 25 grams.

3 × 2 or 5 × 2 mice are used for each does level. Thirty minutes, one hour, two hours, three hours etc. after i.p. injection of test substance, methylphenidate, 60 mg/kg, is injected s.c. At each time interval separate groups of mice were used. After administration of methylphenidate the mice ae placed in the observation cages, 2 in each cage, where they remain for one hour. The cages are placed on corrugated paper, the corrugations facing upwards. It is examined whether or not the mice have been biting the corrugated paper. If not, the substance has had an antagonistic effect. If one or more of the control pairs have also not been biting the corrugated paper the test has to be repeated on a new set of mice. The peak effect was determined for the test substances and also for a number of known neuroleptics.

The other test (2) used for comparision is the catalepsy-inducing effect, which is considered by many workers in the field of pharmacology of neuroleptic drugs to be responsible for the extrapyrimidal symptoms found when using the known neuroleptic drugs. Reference is made to L.Juluo: "On the Interaction between Neuroleptics and Antiparkinson Drugs."Modern Problems of Pharmacopsychiatry, Vol. 5, pg.50-54. The test may be described as follows:

2. As animals are used male Wistar rates weighing 189-220 grams. Five animals are used at each dose level. At least six consecutive dose levels are selected from the following geometrical series: 640, 320, 160, 80, 40, 20, 10, 5, 2.5, 1.25, 0.63, 0.16, 0.08, 0.04 and 0.02 mg/kg body weight.

The test compound is injected subcutaneously (s.c.) Injection volume is 5 ml of the vehicle/kg b.w. Except when otherwise stated saline is used as vehicle.

The animals are brought to the laboratory and kept in groups of five at least 16 hours before the experiment. The animals are placed in the middle of a vertical wire netting (50 cm/49 cm) 60, 120, 180, 240, 300 and 360 minutes after injection of the test compound. The animals are considered cataleptic when they remain immobile during a period of 15 seconds. This cataleptic reaction is designated: + (plus). Untreated animals climb normally up and down the wire netting. The absence of catalepsy is designated: — (minus). The results are expressed as fractions as follows: 0/5, 1/5, 2/5, 3/5, 4/5 and 5/5 in which 0, 1, 2, 3, 4, and 5 represent the number of cataleptic animals out of five (5) animals tested.

Each maximum dose effect - i.e. the strongest effect of each dose irrespective of the hour at which it occurs — is recorded on a data sheet in accordance with the punching instructions forming the basis of the estimation of $ED_{50}$ max., which is based on each maximum dose effect and defined as the dose producing catalepsy in fifty per cent (50%) of the animals.

The two tests were carried out on a number of the novel compounds of Formula I and on a number of closely related thiaxanthene derivatives. As reference drugs were used the three known neuroleptics thiothixene, clopenthixol and flupenthixol in the form of the pure α-isomers which are the most active isomers, the β-isomers being inferior in effect. Moreover some closely related compounds numbered 9, 10 and 11 in the following table. The compounds tested may be represented by the following general formula:

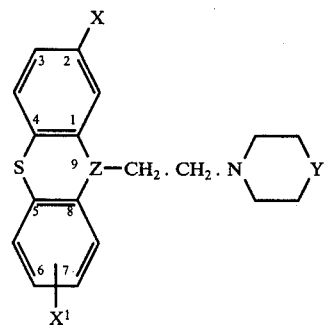

and the results obtained will appear from the following table:

| Substance No. | X | $X^1$ | Z | Y | Methylphenidate antagonism | | | Catalepsy rats mg/kg | Ratio Cat./ Meth. |
|---|---|---|---|---|---|---|---|---|---|
| | | | | | peak effect i.p. | duration of peak effect hours | $ED_{50}$ mg/kg 24 h i.p. | | |
| 1 | $CF_3$ | 6-F | CH . $CH_2$ | >N . $CH_2$ . $CH_2OH$ | 0.04 | 18 | 1.66 | 0.9 | 22 |
| 2 | $CF_3$ | 6-F | CH . $CH_2$ | >N . $CH_3$ | 0.3 | >5 | >10 | 3.1 | 10 |
| 3 | Cl | 6-F | CH . $CH_2$ | >N . $CH_2$ . $CH_2OH$ | 0.8 | >5 | 7.1 | 2.7 | 3.4 |
| 4 | $SO_2N(CH_3)_2$ | 6-F | CH . $CH_2$ | >N . $CH_3$ | 1.0 | ca.17 | >5 | 3.1 | 3.1 |
| 5 | $SO_2N(CH_3)_2$ | 6-F | C=CH | >N . $CH_3$ | 0.4 | >5 | >10 | 1.0 | 2.5 |
| 6 | $CF_3$ | 6-F | C=CH | >N . $CH_2$ . $CH_2OH$ | 0.05 | 18 | 0.24 | 0.12 | 2.4 |
| 7 | Cl | 6-F | C=CH | >N . $CH_2$ . $CH_2OH$ | 0.4 | >5 | >10 | 2.0 | 5 |
| 8 | $CF_3$ | 6-Cl | CH . $CH_2$ | >N . $CH_2$ . $CH_2OH$ | 4.0 | | | >20 | >5 |
| 9 | $CF_3$ | 5-Cl | CH . $CH_2$ | >N . $CH_2$ . $CH_2OH$ | 14 | | | >20 | 1.5 |
| 10 | $CF_3$ | 5-$CF_3$ | CH . $CH_2$ | >N . $CH_2$ . $CH_2OH$ | >10 | | | >20 | |
| 11 | $CF_3$ | 6-$CF_3$ | CH . $CH_2$ | >N . $CH_2$ . $CH_2OH$ | >10 | | | >20 | |
| 12 | $SO_2N(CH_3)_2$ | 6-F | C=CH | >CH . $CH_2$ . $CH_2OH$ | 0.87 | | >10 | 0.69 | 0.8 |
| 13 | $CF_3$ | 6-F | C=CH | >CH . $CH_2$ . $CH_2OH$ | 0.03 | 48–72 | 0.03 | 0.05 | 1.7 |
| 14 | $CF_3$ | 6-F | CH . $CH_2$ | >CH . $CH_2$ . $CH_2OH$ | 0.25 | | 3.6 | 0.21 | 0.8 |
| 15 | Cl | 6-F | C=CH | >CH . $CH_2$ . $CH_2OH$ | 0.08 | | 0.27 | 0.07 | 0.9 |
| Thio- | $SO_2N(CH_3)_2$ | H | C=CH | >N . $CH_3$ | 0.4 | | >40 | 0.06 | 0.14 |

| Substance No. | X | $X^1$ | Z | Y | Methylphenidate antagonism peak effect i.p. | duration of peak effect hours | $ED_{50}$ mg/kg 24 h i.p. | Catalepsy rats mg/kg | Ratio Cat./ Meth. |
|---|---|---|---|---|---|---|---|---|---|
| thixene α-Clopenthixol | Cl | H | C=CH | >N . $CH_2$ . $CH_2OH$ | 0.7 | 5 | >40 | 0.45 | 0.7 |
| α-Flupenthixol | $CF_3$ | H | C=CH | >N . $CH_2$ . $CH_2OH$ | 0.07 | 6 | 17 | 0.12 | 1.74 |

From the table it is obvious that the ratio catalepsy/methylphenidate antagonism is much improved when going from other cats, -substituted derivatives to 6-fluoro substitution, especially within the piperazine type compounds, when comparing substances 1 and 8 the only difference being the kind of halogen substitution in position 6, the methylphenidate antagonism is about one hundred times better in 1 than in 8 and the ratio about four times better. The two wellknown neuroleptics clopenthixol and flupenthixol have ratios between 0.7 and 1.74 well within the range of other known neuroleptics. It may be mentioned that the neuroleptic chloropromazine has cataleptic activity of 4.0 and methylphenidate antagonism of 4.0 giving a ratio of 1.0.

When comparing substances 1 and 6 with α-flupenthixol it is apparent that while the peak effect of methylphenidate antagonism is of the same order of magnitude, the duration of peak effect is much improved, and for compound 6 even after 24 hours a considerable antagonism still exists. The most surprising effect, however, is seen with Substance No. 13 where the duration of peak effect is about 2–3days and the peak effect is still unchanged 24 hours after injection.

The compounds of Formula I and the non-toxic acid addition salts thereof may be administered to animals such as dogs, cas, horses, sheeps or the like, including human beings, both orally and parenterally, and may be used for example in the form of tablets, capsules, powders, syrups or in the form of the usual sterile solutions for injection. Results upon administration to human beings have been very gratifying.

Most conveniently the compounds of Formula I are administered orally in unit dosage form such as tablets or capsules, each dosage unit containing a non-toxic acid addition salt of one of the said compounds in an amount of from about 0.05 to about 50 mg, most preferably, however, from about 0.5 to 25 mg, calculated as the free amine, the total daily dosage usually ranging from about 0.5 to about 300 mg. The exact individual dosages as well as daily dosages in particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

When the compound of Formula I is an ester, preferably a decanoic acid ester of palmitic acid ester, the composition may advantageously be an oily solution for injection, and such solutions often have a very prolonged effect when compared with the corresponding unesterified compound.

Typical examples of formulas for compositions containing 2-trifluoromethyl-6-fluoro-9-(3-(4-(2-hydroxyethyl)-piperazine-1-yl(propyl)-thiaxanthene (called Lu 10-022 for short) as the active ingredient are as follows:

1. Tablets containing 1 milligram of Lu 10-022 calculated as the free base in the form of the dihydrochloride;
 Lu 10-022; 1 mg.
 lactose; 37 mg.
 potato starch; 74 mg.
 gelatine; 2 mg.
 talcum; 8 mg.
2. Solution for injection containing per ml:
 Lu-10-022; 0.5 mg.
 sodium chloride; 0.9 mg.
 sterile water ad; 1 ml.
3. Syrup containing per milliliter:
 Lu 10-022; 0.2 mg.
 methyl-paraben; 1.0 mg.
 propyl-paraben; 0.1 mg.
 saccharose; 400 mg.
 water; ad 1 ml.
4. Capsules containing per capsule:
 Lu 10-022; 2 mg.
 lactose; 40 mg.
 magnesium stearate; 0.5 mg.

Any other pharmaceutical tableting adjuvants may be used provided that they are compatible with the active ingredient, and additional compositions and dosage forms may be similar to those presently used for neuroleptics such as thiothixene, clopenthixol or flupenthixol. Also combination of the compounds of Formula I as well as their non-toxic acid salts with other active ingredients, especially other neuroleptics, thymoleptics, tranquilizers or the like, fall within the scope of the present invention.

As previously stated, when isolating the compounds of Formula I in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartrates, or bitartrates, embonates and maleates of the amines of Formula I. Other acids are likewise suitable and may be employed if desired. For example; fumaric, benzoic, ascorbic, succinic, salicyclic, bismethylenesalicyclic, propionic, gluconic, malic, malonic, mandelic, cinnamic, cintraconic, stearic, palmitic, itaconic, glycolic, benzenesulphonic, and sulphamic acid may also be employed as acid addition saltforming acids. When it is desired to isolate a compound of the invention in the form of free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalities of animals by administering to a living animal body, including human beings, an adequate quantity of a compound of Formula I or a nontoxic acid addition salt thereof. An adequate quantity would be from about 0.001 mg to about 1 mg per kg of body weight in each unit dosage and from about 0.003 milligrams to about 3 milligrams/kg of body weight per day.

It is to be understood that the invention is not limited to the exact details of operation or exact compound or compositions shown and described, as obvious modifications and equivalents will be apparent to one skilled in the art.

We claim:

1. A compound of formula

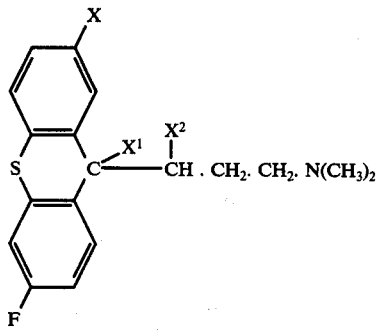

wherein X is selected from the group consisting of —$CF_3$ and —$SO_2.N(CH_3)_2$, and $X^1$ and $X^2$ form together a single bond.

2. A compound of the formula

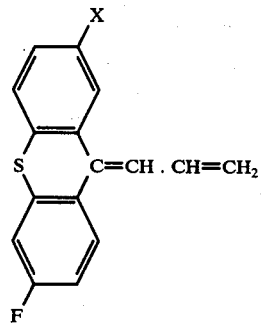

wherein X is selected from the group consisting of —$CF_3$ and —$SO_2.N(CH_3)_2$.

3. The compound 2-trifluoromethyl-6-fluoro-9-(3-dimethylaminopropylidene)-thiaxanthene.

4. The compound 2-trifluoromethyl-6-fluoro-9-(2-propenylidene)-thioxanthene.

* * * * *

UNITED STATES PATENT OFFICE
CERTIFICATE OF CORRECTION

Patent No. 4,044,024         Dated Aug. 23, 1977

Inventor(s) Buus et al

It is certified that error appears in the above-identified patent and that said Letters Patent are hereby corrected as shown below:

Col. 8, line 66; "evaporated," should read --evaporated.--
Col.10, line 41; "thiazanthene" should read --thiaxanthene--
Col.10, line 45; "thiazanthene" should read --thiaxanthene--
Col.10, line 55; "thiazanthene" should read --thiaxanthene--
Col.10, line 63; "thiazanthene" should read --thiaxanthene--
Col.10, line 67; "thiazanthene" should read --thiaxanthene--
Col.11, line 31; "ws" should read --was--
Col.11, line 36; "thiazanthene" should read --thiaxanthene--
Col.11, line 39; "thiazanthene" should read --thiaxanthene--
Col.12, line 23; "thiazanthene" should read --thiaxanthene--
Col.12, line 27; "thiazanthene" should read --thiaxanthene--
Col.12, line 37; "thiazanthene" should read --thiaxanthene--
Col.12, line 43; "thiazanthene" should read --thiaxanthene--
Col.12, line 48; "thiazanthene" should read --thiaxanthene--
Col.15, line 27; "ae" should read --are--
Col.17, line 15; "cats" should read --6--
Col.17, line 52; "in particular" should read --in a particular--
Col.18, line 56; "cintraconic" should read --citraconic--

Signed and Sealed this

Twenty-eighth Day of March 1978

[SEAL]

Attest:

RUTH C. MASON
Attesting Officer

LUTRELLE F. PARKER
Acting Commissioner of Patents and Trademarks